(12) United States Patent
Mauchamp et al.

(10) Patent No.: US 6,537,224 B2
(45) Date of Patent: Mar. 25, 2003

(54) MULTI-PURPOSE ULTRASONIC SLOTTED ARRAY TRANSDUCER

(75) Inventors: Pascal Mauchamp, Fondettes (FR); Aimé Flesch, Andrésy (FR)

(73) Assignee: Vermon, Tours Cedex (FR)

( * ) Notice: Subject to any disclaimer, the term of this patent is extended or adjusted under 35 U.S.C. 154(b) by 0 days.

(21) Appl. No.: 09/876,110

(22) Filed: Jun. 8, 2001

(65) Prior Publication Data

US 2002/0188200 A1 Dec. 12, 2002

(51) Int. Cl.[7] ............................................. A61B 8/00
(52) U.S. Cl. ........................ 600/459; 600/437; 29/25.35
(58) Field of Search ................................ 600/459, 443, 600/439, 437; 29/25.35

(56) References Cited

U.S. PATENT DOCUMENTS

| 3,952,216 A | 4/1976 | Madison et al. |
| 4,097,835 A | 6/1978 | Green |
| 4,492,120 A | 1/1985 | Lewis et al. |
| 5,195,519 A | 3/1993 | Angelsen |
| 5,492,126 A | 2/1996 | Hennige et al. |
| 5,558,092 A | 9/1996 | Unger et al. |
| 5,651,365 A * | 7/1997 | Hanafy et al. ............... 600/459 |
| 5,724,976 A * | 3/1998 | Mine et al. .................. 600/459 |
| 5,769,790 A | 6/1998 | Watkins et al. |
| 5,938,612 A * | 8/1999 | Kline-Schoder et al. ..... 310/334 |
| 5,957,851 A | 9/1999 | Hossack |
| 6,050,943 A | 4/2000 | Slayton et al. |
| 6,160,340 A * | 12/2000 | Guo et al. ................... 310/334 |

* cited by examiner

*Primary Examiner*—Francis J. Jaworski
*Assistant Examiner*—William C. Jung
(74) *Attorney, Agent, or Firm*—Larson & Taylor, PLC

(57) ABSTRACT

An ultrasonic probe is provided for medical applications which can be used both in high resolution imaging and therapy or other high intensity applications. The probe includes a primary ultrasonic transducer array operating at first resonant frequency and formed by a plurality of elements arranged linearly along a coordinate axis, and a secondary ultrasonic transducer array operating at second resonant frequency and comprising a plurality of elements arranged linearly along the coordinate axis and being interdigitated with the elements of the primary ultrasonic transducer array. In one embodiment, separate transducer units are joined to form the probe while in a further embodiment, the two arrays are produced from a common piezoelectric member.

33 Claims, 1 Drawing Sheet

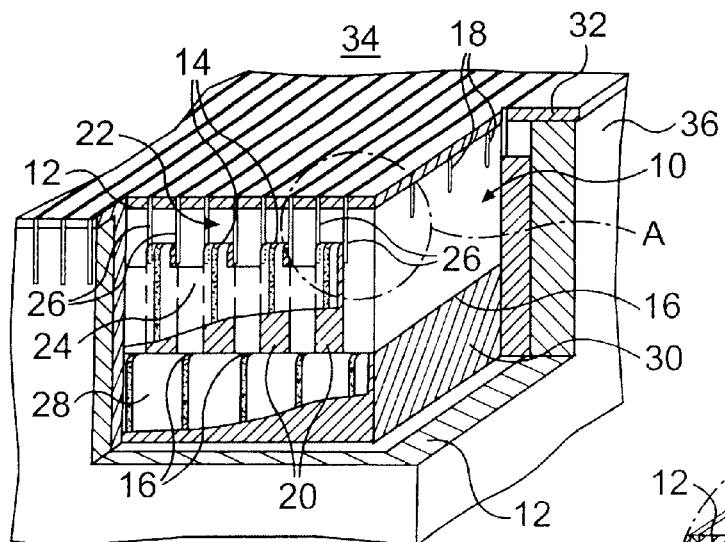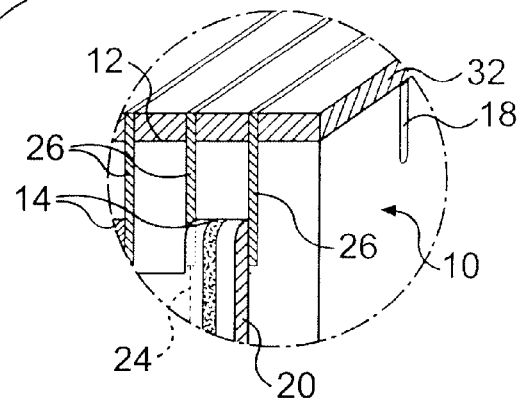
FIG. 1
FIG. 1A
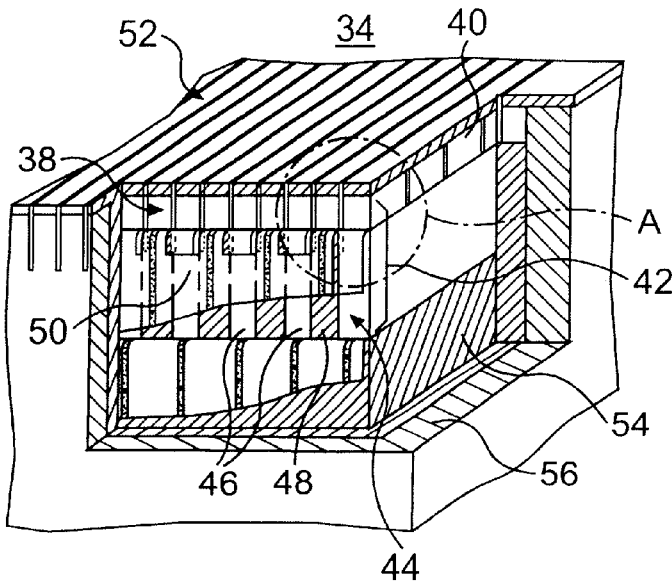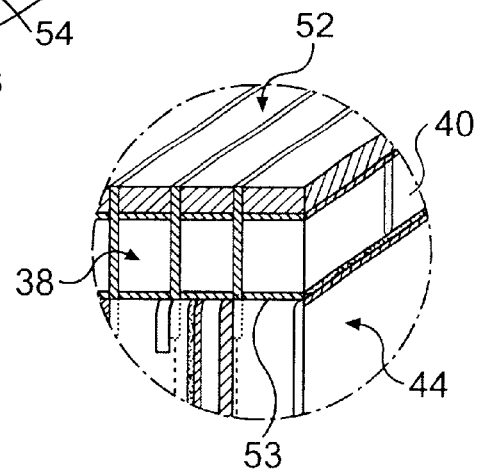
FIG. 2
FIG. 2A

MULTI-PURPOSE ULTRASONIC SLOTTED ARRAY TRANSDUCER

BACKGROUND OF THE INVENTION

1. Field of the Invention

The present invention relates to ultrasonic imaging probes designed for medical applications, and, more particularly, to an improved probe wherein diagnosis and high intensity ultrasound modalities are combined in the same apparatus.

2. Related Art

Ultrasound is used in many different domains for purposes of inspection and medical diagnosis. Transducers capable of sending and receiving ultrasonic energy are commonly made from a piezoelectric material such as a ceramic, crystal or co-polymer which reacts to produce an output in response to electrical or mechanical stress. Until now, imaging modalities are often segregated from Doppler, therapy or treatment modalities because low intensity ultrasound propagating at high frequency is highly attenuated by the tissue being diagnosed and this results in low efficiency Doppler operation. Such low intensity, high frequency ultrasound produces no therapeutic or damaging (non-ionizing) effects on the tissue under test and because of this non-ionizing characteristic, ultrasound is the preferred diagnostic modality for fetus and pediatric applications.

Another factor which governs ultrasonic transducer characteristics is the energy transfer of the ultrasonic transducer device. In this regard, the energy conversion factor of the transducer device is substantially constant and depends on the type of piezoelectric material employed therein. Thus, a balancing exercise must be used by the designer in determining the best compromise between bandwidth and transducer sensitivity. Otherwise, most transducers can be designed to exhibit broad bandwidth operation but only at the expense of low sensitivity in that frequency range.

Typically, an imaging ultrasonic transducer has maximum bandwidth (obtained through the use of low quality factor piezoelectric material) in order to cover the expanded frequency range of the signal being returned through the propagation medium. Moreover, the higher the frequency of transducer, the better the image. When the transducer is used in Doppler operation, the frequency of transducer should be determined based on the velocities of the test object and the depth of the region to be explored. In general, the Doppler frequency is always lower than the associated imaging frequency so as to improve the sensitivity of the received signals.

With regard to high intensity ultrasound, if a therapeutic effect is to be produced in the sonified region, the power of the transmitted ultrasonic energy must be increased in proportion, thereby resulting in heating of the region of tissue of concern. Because conventional imaging transducers are designed with a maximized bandwidth, the application of high power electrical energy to the low quality factor-based transducers used for imaging will rapidly destroy the corresponding transducer because of excessive heating of the transducer core. As a consequence, considering the situation described above, supplying high intensity ultrasonic energy to the tissue under diagnosis dictates the use of a transducer of a particular construction, e.g., a transducer made from high quality factor piezoelectric material, as well as lowering of the frequency used, and, if necessary, cooling of the active transducer material by addition of a heat-sink or an active cooling system.

A further aspect of the application of ultrasound which was not discussed above concerns the new advanced imaging mode referred to as harmonic imaging. In this mode, the transducer must be capable of emitting ultrasound at a fundamental frequency and receiving returned echoes at two, or more, times this frequency. Further, in the case where contrast agents are injected in the blood flow, the transducer must be driven to produce a high power emission in order to collapse micro-bubbles in the contrast agents prior to receiving non-linear responses from the region of interest. It is preferable to control collapsing of the contrast agents by using another transducer operated at a lower frequency specifically tailored for this purpose.

It will be understood from the foregoing that implementing different modalities, such as imaging, Doppler or therapy operations, requires many changes between various probes. This is time consuming and, furthermore, is sometimes impossible, as a practical matter, when scanning of the image is required in guiding the operation to be carried out.

The prior art includes a number of references wherein plural functionalities are combined in the same transducer probe. In U.S. Pat. No. 4,492,120, to Lewis et al., a transducer assembly is provided which comprises separate imaging and Doppler transducers. Each transducer is independently damped according to the performance criteria of the corresponding function. The imaging transducer may be of a linear array type and the Doppler transducer is assembled on the sides of the imaging transducer. Such a construction results in a significant increase in the length of the resultant transducer device and further, the Doppler acoustic pattern is not necessarily included in the image. In general, this concept has now been abandoned and replaced by a technique wherein an array of elements are driven as Doppler transmitter—receivers alternately with an imaging mode of operation.

In U.S. Pat. No. 5,195,519 to Angelsen, a dual function probe is provided, similarly to the Lewis et al. patent. In one of the aspect of the Angelsen patent, the probe is comprised of a steering transducer having double emitting faces. Each face is supplied with a selected frequency so as to be compatible either with an imaging mode or with a Doppler mode. This construction is limited to single element transducers and requires a coupling bath to be operable.

U.S. Pat. No. 4,097,835, to Green, discloses a moving pair or set of focused transducer members which are movable along linear paths. Each transducer member is of a semi-circular shape so the pair taken together forms a circular surface. A first semi circular transducer can be used for B-mode imaging while the second is dedicated to Doppler functions. Because the transducers are completely separated, interference between signals produced during the imaging and Doppler modes can be avoided. However, such a configuration results in a dramatically inferior lateral resolution of the image as well as in substantially inferior Doppler spatial measurements.

U.S. Pat. No. 3,952,216, to Madison et al., discloses a multi-frequency transducer including a first transducer array operating at low frequency and a second transducer array operating at high frequency. The second transducer array is located at the front of device with the first transducer array being disposed there behind. For both transducer arrays, the arrays are formed by a plurality of single elements connected in parallel, and each single transducer element is formed by sandwiching together a plurality of piezoelectric layers. The high frequency transducer array, is used in transmitting high frequency waves in the propagating medium while the low frequency transducer array is dedicated to reception of the low frequency response obtained from the difference of the two consecutive transmitted pulses. Ultrasonic transducers of this type are well adapted for sonar (underwater) applications where the bandwidth is very narrow and sensitivity must be absolutely preserved. However, such transducers are not suitable for high resolution imaging applications and do not employ a multi-element construction.

A further multi-layer transducer construction is disclosed in U.S. Pat. No. 5,957,851, to Hossack, wherein the transducer is comprised of first and second piezoelectric layers, and the second layer is disposed on the first layer. The first and second layers are separately driven and signals from one, or the other, may be isolated each other. The combination of the two layers enables transmission of ultrasonic waves that are controlled in frequency. Echoes returned from the area of examination can be analyzed by either the first or the second piezoelectric layer or by a combination of the two lawyers. The electrical connections of the piezoelectric layers are also described in the patent. However, the transducer as described in the patent requires that the associated system be equipped with driving electronics compatible with a switching layer device, in that, otherwise, when only one of the layers is used for the reception of echoes, acoustic waves propagating through the other layer will create interference that dramatically degrades the pulse shape of the echoes.

U.S. Pat. No. 5,558,092, to Unger, discloses a method for performing a diagnostic ultrasound operation simultaneously with the application of therapeutic ultrasonic waves. A therapeutic array transducer is located at a central region of the overall array and is surrounded by the imaging transducer array. The transducer array are not necessary disposed in a linear arrangement and can be arranged in a matrix or as a combination of annular and linear array, or like confirmations. Typically, the therapeutic transducer array operates at a lower frequency than the imaging transducer array and serves as a high intensity ultrasound transmitter while the imaging transducers are used in both transmitting and receiving operations. This approach is useful in high intensity ultrasound energy applications but the image obtained is affected by the missing zone corresponding to that occupied by therapeutic transducer surface, and further, the dimensions of the array are significantly increased and thus may cause discomfort, in use, to the patient or operator.

In U.S. Pat. No. 5,769,790, to Watkins et al., an ultrasonic device is provided which comprises a combination of a therapy focused transducer and a imaging phased array transducer. In one configuration, the imaging array transducer is located at the center of the hemispherical therapy transducer, and in another configuration, the two transducers are mounted in the same plane, one next to the other. This device is capable of delivering the high acoustic energy necessary to raise by several degrees the temperature of the tissue being examined. The chief drawback of this approach is the large dimension or surface area of the resulting device. In this regard, the focal length of the therapy transducer is predetermined by the surface shape of transducer so that the transducer device must be moved according to the location of the area of interest. Very similarly, U.S. Pat. No. 5,492,126, to Hennige et al, relates to a probe comprising a combination of therapy and imaging scanning transducers. Both transducers can be single element transducers or array devices. Each transducer has a specific geometry based on the particular application and the transducers are placed one next to the other. This configuration has large dimensions and thus requires additional room to be installed.

U.S. Pat. No. 6,050,943, to Slayton et al., discloses an air-backed transducer array assembly capable of simultaneously generating high power ultrasound, forming an image of the area of interest and monitoring the temperature of the tissue being sonified. The transducer assembly is equipped with a fluid cooling system mounted on the front face of the transducer. The ultrasonic transducer assembly is said to be useful in a combined diagnostic-therapy modality. However, performing all operations with the same ultrasonic device requires that the system alternately supply the area of interest with either low intensity, wide bandwidth signals or high intensity, narrow bandwidth signals and it would appear to be difficult to reconcile the two modes of operation. Furthermore, the patent does not address a potential compatibility problem with respect to piezoelectric material used. Commonly, as indicated above, ceramics suitable for high power applications are not suitable for imaging operations and vice versa. Finally, if a compromise is made with respect to the material used, this can lead to excessive heating of the device when used in a High Intensity Focused Ultrasonic (HIFU) mode, whereas when used in the imaging mode, the quality of image produced will be weaker than that provided by standard transducer devices available in the marketplace.

SUMMARY OF THE INVENTION

To overcome drawbacks set forth above, there is provided, in accordance with the present invention, a multipurpose ultrasonic transducer for general use both in high resolution imaging and in therapy or other high intensity applications. In general, the ultrasonic transducer apparatus is constructed as a sandwich of two transducer arrays, each having a respective resonance frequency so the transducer apparatus can be operated and controlled as a single layer transducer or as a multilayer transducer. The ultrasonic probe formed by the transducer apparatus is of a construction that enables the probe to be of compact size and to offer superior electro-acoustic performance in comparison with conventional prior art ultrasonic probes.

In accordance with a first aspect of the invention, an ultrasonic probe is provided for use in combined imaging/therapy or in a HIFU mode or system. The transducer is comprised of a first imaging transducer array operating at a first frequency and a second transducer array operating at a second frequency, the first and second transducer arrays being integrated in an inter-digital manner and having approximately the same acoustic aperture, so that the system control software is simplified.

In accordance with a second aspect of the invention, an ultrasonic probe is provided which is comprised of a transducer unit comprising a first transducer array having a first thickness and a second transducer array attached to a rear or back surface of the first transducer and having a second thickness, the transducer unit having a thickness corresponding to the sum of the thickness of the first transducer array and the thickness of the second transducer array. The polarities of the first and second transducer arrays can be reversed in order to enhance the electrical impedance of device.

In accordance with a third aspect of the invention, the first transducer array and the second transducer array are produced from a common original piezoelectric member, and each transducer array is formed to have a thickness corresponding to its array frequency.

Finally, in all of the above aspects of the invention, the first and second transducer arrays are independently connected to the respective system cables therefor and can thus be separately addressed by the system.

Among other advantages, an ultrasonic probe as set forth above is capable of simultaneously performing high resolution imaging processes as well as steering and focusing high intensity ultrasonic energy in the area of interest. The interdigitated integration of the two arrays provides a powerful approach to driving the transducer electronically, in that the same delay lines can be used for one array and the other array without any inconvenience. According to the transducer construction, separating two adjacent high intensity transducer elements with an imaging transducer element therebetween significantly increases the thermal dissipation of the particular array being excited, and further, cross-coupling between elements is also dramatically reduced, thereby improving the overall quality of system.

Ultrasonic devices in accordance with the invention can be specifically constructed for performing diagnoses of images combined with either drug delivery, or harmonic imaging, or HIFU operation.

Further features and advantages of the present invention will be set forth in, or apparent from, the detailed description of preferred embodiments thereof which follows.

BRIEF DESCRIPTION OF THE DRAWINGS

FIG. 1 is a perspective view, partially broken away, of a first preferred embodiment of the transducer probe device of the invention;

FIG. 1A is a detailed view drawn to an enlarged scale of region A of the device of FIG. 1;

FIG. 2 is a perspective view, partially broken away, of a second preferred embodiment of the transducer probe device of the invention; and FIG. 2A is a detailed view, drawn to an enlarged scale, of region A of the device of FIG. 2.

DETAILED DESCRIPTION OF THE PREFERRED EMBODIMENTS

Before turning to the drawings, it is noted that, ultrasonic transducer arrays assigned for medical applications are often slotted devices where a plurality of transducer elements are linearly arranged. These transducers are acoustically isolated each other to as high a degree as possible by filling the slots or interstices between the transducers with an attenuating material such as a flexible resin or a diffusing material such as microbubbles embedded into a resin mixture. Each transducer element of the slotted transducer device is individually addressed electrically and signal phasing is then applied to the acoustic aperture to provide a synthetic focused acoustic field. In general, a group of elements constitutes an acoustic aperture and the aperture "slides" along the transducer array during the scanning process. By controlling the signal phasing of the excitation, steering of the acoustic pattern can be achieved.

The array transducer of the present invention is, in principle, a combination of at least two transducer arrays superimposed on each other such as is done in inter-digital devices. The respective arrays so produced can have the same frequency, or different frequencies, with the frequency being selected based on the type of application for which the transducer array is to be used. The transducer characteristics can also individually be modified to fit any customized acoustic specifications. In the preferred embodiments discussed below, the ultrasonic transducer device of the invention is described as being of the phased array type but as will be obvious to those skilled in the art, the invention can also be applied to a linear array or any shaped, curved or flat surface transducer array.

In the first preferred embodiment of the invention described below, the ultrasonic probe is designed for operation at both high and low frequencies and over selected bandwidths. As will be described, the device is basically comprised of a primary array transducer (PAT) having a first thickness and a secondary array transducer (SAT) having a second thickness. The ratio of the thicknesses of the primary and secondary transducers is determined according to the clinical application for which the probe is to be used. For example, in harmonic imaging, this ratio can advantageously be about 2, in order to separate the spectral response of the transmit element from those of the receive elements.

Referring to FIG. 1, a piezoelectric member 10 is shown which is machined in a bulk shape having two opposite parallel main faces. Piezoelectric member 10 can be made of a polycrystalline ceramic, a ceramic-polymer composite, a piezoelectric single crystal, a single crystal-polymer composite or the like. Preferably, the pole direction is perpendicular to the main opposite surfaces of the piezoelectric member 10.

A front electrode 12 is deposited on the front main surface and a pair of rear electrodes 14 and 16 deposited so as to create an electrical field when the piezoelectric material is subjected to electrical excitation. The electrodes 12, 14 and 16 may be made of any metal having high electrical conductivity so as to reduce parasitic resistance in the associated electrical circuit. However, the preferred candidates for use in making electrodes 12, 14 and 16 are copper, silver or aluminum materials that ensure superior electrical conductivity. Further, the adherence of the electrodes 12, 14 and 16 to the respective faces of member 10 on the faces can be greatly improved by sputtering a sub-coating of palladium or chromium prior to electrode deposition.

As shown in FIG. 1, the piezoelectric member 10 is partially split along the azimuthal axis by spaced grooves 18. Grooves 18 are preferably filled with a flexible or low Poisson coefficient resin in order to combat Lamb waves produced by transducer vibrations. Grooves 18 are designed to provide broadening the bandwidth of transducer operation. It is important to note that the grooves 18 are preferably performed prior to the electrode deposition.

After grooves 18 are formed, electrode 12 is deposited on the front surface of the piezoelectric member 10, and, on the rear face of the said piezoelectric member 10, relatively large grooves 20 are formed in the elevational direction. Grooves 20 have dimensions and a pitch (spacing) according to transducer array specifications, and, in particular, grooves 20 are formed in such a manner to obtain a remaining thickness or relative raised portion, indicated at 22. The grooves 20 produce a resultant thickness of member 10 which corresponds to the frequency of the PAT. In other words, the original thickness of the piezoelectric member 10 corresponds to that of the SAT and the resultant thickness produced in forming grooves 20 governs the frequency of the PAT.

In the next step, the back surface electrodes 14 and 16 mentioned above are deposited on the machined piezoelectric member 10. It will be appreciated that whatever technique is used for electrode deposition of electrodes 14 or 16 on the rear surface of the piezoelectric member 10, there is a risk of covering all of the surfaces and thus shunting the electrodes from adjacent elements. The following description will describe how to avoid shunting of electrodes.

At this stage of the manufacturing process, flexible (flex) circuit 24 is then bonded onto the recessed surfaces formed by the bottom surface of the grooves of the PAT thickness 22. As can be better seen in the FIG. 1A, flex circuit 24 does not need to entirely cover the surface of electrode, and usually a covering of only few millimeters deep is sufficient to achieve good electrical contact. Further, this approach greatly simplifies the bonding process.

Once the flex circuit 24 is assembled to the PAT, cuts 26 are made. The cuts 26 are provided at regular intervals along the elevational direction. In the embodiment presently under consideration, the cuts 26 must be made in alignment with the edges of grooves 20, as shown, and, additionally, the cuts 26 must emerge tangentially with respect to the walls of the corresponding grooves 20. This operation will not only separate the electrodes 14 from the elements of each transducer array but will also split the flexible circuit 24 so as to completely insulate each transducer element. It will understand that attention must be paid to providing full alignment between cuts 26 and grooves 20 to achieve these results. The cuts 26 are preferably performed using a diamond blade having thickness in the range from 40 to 80 $\mu$m in order to make feasible such alignment.

The next step of the manufacturing process involves filling of the voids formed by grooves 20. Preferably, a filling of flexible resin such as a mineral particle filled epoxy resin is used. However, resins belonging to the silicon, polyurethane or soft epoxy families may also be suitable, and plastic or metallic particles are also good candidates for the filling mixture. During the filling operation, the electrode pattern of the secondary frequency transducer should be masked by an adhesive film so the excess resin laid thereon may be easily removed afterward. The filled grooves 20 act to provide a backing effect for the PAT. It will be understood that transducer bandwidth increases with the impedance of the backing member but sensitivity proportionally decreases in the same manner.

At this stage, a further flex circuit 28, which is to be attached to the SAT, is assembled on the rear face of the apparatus. This operation is much easier than that regarding assembly of the PAT flex circuit 24 in that the flex circuit 28 can be laid so as to entirely cover the surface of the SAT with no influence on the acoustic characteristics.

Finally, a second backing block 30 is affixed to the piezoelectric member 10 to complete the transducer assembly. It is important to note that backing 30 affects only the behavior of the SAT, so that blocking block 30 should be chosen with respect to the desired characteristics of the device. Generally speaking, the SAT simply has to be back-loaded by very light impedance member so as not to disturb the quality factor of the piezoelectric. Suitable backing compositions for blocking block 30 include a mixture of epoxy resin and hollow particles such as plastic microbubbles.

In accordance with common practice, the front face of the ultrasonic transducer is equipped with acoustic matching layers 32 to enhance the energy transfer between the piezoelectric material of the member 10 and the propagation medium 34. This feature is of particular importance when transducer is designed for use in biologic tissues where the examination of the acoustic impedance mismatch is greater. It will be evident that the use of the two transducer arrays of different frequencies requires that a particular matching layer be employed for each. In practice, only the transducer designed for imaging needs to be front matched, so that the characteristics of the matching layer 32 described above are determined based on the characteristics of the high frequency transducer (PAT) whereas layer 32 acts as a protective layer for the SAT. In certain cases, especially when the frequency ratio between the different frequencies is compatible, the double matching layer provided for the PAT device can be advantageously considered as a single matching layer for the SAT device.

To complete the construction of the apparatus shown, the piezoelectric member as set forth above is surrounded by a potting material 36 in order to maintain all elements in place. Further, shielding for the device can be provided over the potting surface. Moreover, a silicon lens (not shown) can be provided on the front surface of the resultant transducer in order to provide transverse focusing.

In the second preferred embodiment of the invention shown in the FIGS. 2 and 2A, as in the embodiment of FIG. 1, at least two array transducers are assembled and are independently addressed. The primary array transducer (PAT) operates at higher frequency and is devoted to imaging applications while the secondary array transducer (SAT) is used for complementary functions appear such as therapy, drug delivery or harmonic imaging (collapsing of microbubbles). As well appear, the method of construction of the second preferred embodiment is significantly different from that described above for the first preferred embodiment. Some similar elements to those shown in FIG. 1 have been given the same reference numbers in FIG. 2.

Preferably, the PAT, which is generally denoted 38, is produced from a first plate or member 40 of piezoelectric material, and the secondary, integrated or overlapping array transducer SAT, which is indicated by bracket 42, is formed by adding a complementary piezoelectric plate 44. Plate 44 is of a sandwich construction comprised of piezoelectric walls 46 and polymer filled slots or kerfs 42, also referred to below as polymer layers.

The overall construction of the ultrasonic probe of the second preferred embodiment is best understood by reference to FIG. 2, where the piezoelectric member 40 is preferably plate shaped as shown in FIG. 2 and has a thickness governed by the resonance frequency of PAT 38. The transducer elements of PAT 38 are formed by individual, spaced slots 26 having a pitch corresponding to one-half of the final pitch of the array.

The rear face of the piezoelectric member 40 is electrode plated as described above and a flex circuit 50 is assembled thereon in order to provide an electrical connection to the corresponding electrical cable.

The PAT 38 is then formed by addressing only even or odd elements of the array so that, as a result, two adjacent active elements are separated by a single identical passive element. This method provides excellent cross coupling isolation for the array.

The front (upper) face of the PAT 38 is equipped with matching layer set 52 corresponding to that described above in order to enhance the energy transfer between the piezoelectric member 40 and the propagation medium 34. For simplicity of fabrication, the characteristics of the matching layers of set 52 are determined according to the frequency of the PAT elements located just beneath the layers. The matching layer material of the matching layer set 52 can also be selected from among those families of polymers or particle filled polymers exhibiting an acoustic impedance between those of the piezoelectric member 40 and propagation medium 34.

Considering the construction of the SAT 42 in more detail, the SAT 42 is prepared as a multilayer sandwich wherein the piezoelectric layers or walls 46 are sandwiched with the identical polymer layers filling slots 48 so as to form a slotted piezoelectric unit wherein piezoelectric regions are regularly spaced apart by insulated regions formed by polymer layers 48. One common technique for making such a transducer sandwich is to align piezoelectric plates of a predetermined thickness at regularly spaced intervals and then fill the spaces or voids therebetween with a polymer or resin. After curing, grinding of all surfaces is used to obtain the desired transducer array block.

Other techniques are also available for use such as a "split and fill" technique using a diamond saw to obtain piezoelectric walls 46 and then filling the spaces between the walls to form layers 48, or a molding technique where the wall pattern is produced by a ceramic molding process, and the ceramic pattern is then cured at high temperature to remove organic matter. The polymer filler may then be added by pouring or molding or injection molding with no influence on the manufacturing process.

In the next step, the slotted piezoelectric unit 40 is then electrode plated on the piezoelectric surface thereof by masking the polymer filled regions. The electrodes correspond to the "forward" and "backward" electrodes, respectively. The forward electrode, which is denoted 53 in FIG. 2A, is oriented toward the propagation direction while the backward electrode contacts with the backing member.

In a further step in the process, the transducer block or unit is assembled to the rear face of the PAT 38. It will be understood that because the PAT and the SAT devices 38 and 42 are joined in an inter-digital fashion, this assembly operation must be carried out with care, in order to perfectly align the piezoelectric elements of the SAT 42 to the non-connected elements of the PAT 38.

The array transducer resulting from this process is a multilayer device comprising a first piezoelectric layer 46 having first thickness and a second piezoelectric layer 40 having a second thickness. In one preferred embodiment, the first thickness and the second thickness are chosen to be equal to each other in order to simplify the control of final resonance frequency. In the case of a multilayer transducer, the middle electrode preferably is selected to be the common electrode of transducer, while external or end electrodes are used for the "hot" signals being applied thereto. The implementation of the stacked transducers for the SAT must be accompanied with an extension of the middle electrode as the electrical ground plane and the external electrodes as signal tracks; it is noted that the opposite electrodes of the stacked elements are connected together to provide the transducer with an extensional operating mode.

The transducer construction just described is particularly suitable for harmonic imaging applications wherein control of the bandwidth and the transmit frequency is required in both cases.

In accordance with another aspect of the invention, the thickness of the front piezoelectric layer is designed to be different than the thickness of the back piezoelectric layer of the device and the SAT preferably operates using the back piezoelectric layer as vibrating member and the front piezoelectric layer as the matching layer in order to enhance conversion performance. In addition, sub-dicing (not shown) can be performed on the front piezoelectric layer so as to decrease the acoustic impedance of the material in order to optimize the energy transfer by lowering reflections at the transducer interface. Such sub-dicing can be carried out either entirely, or partially, in the thickness of the front piezoelectric layer without inconvenience. The slots or slits produced by such sub-dicing are filled with attenuating resin to complete the construction.

Finally, a backing member or backing 54 is assembled to the rear face of the secondary transducer 42. It is important to note that the passive, filled grooves 48 of the secondary transducer 42 act as backing members with respect to the primary array transducer 38, so the backing 54 may be specifically defined for each type of transducer without influencing the basic fabrication process. To complete the construction of the apparatus, a housing 56 is provided in the form of an encapsulating potting material.

In the above descriptions, the focus has been on a dual array transducer apparatus for combined use in diagnostic and therapy or drug delivery applications. However, as was indicated previously, it should be understood that the number of transducers of the transducer apparatus is not limited to two and that, for example, the multilayer device described in connection with the second embodiment (FIG. 2) may have the primary layer made up of a ceramic, composite, semi-composite or single crystal and the secondary layer may also be made up of a ceramic, composite, semi-composite or single crystal.

Although the invention has been described above in relation to preferred embodiments thereof, it will be understood by those skilled in the art that variations and modifications can be effected in these preferred embodiments without departing from the scope and spirit of the invention.

What is claimed is:

1. An ultrasonic probe for medical applications, said probe comprising:
   (a) a primary ultrasonic transducer array adapted to operate at a first resonant frequency and comprising a plurality of individual transducer elements arranged linearly along a coordinate axis;
   (b) a secondary ultrasonic transducer array adapted to operate at a second resonant frequency and comprising a plurality of individual transducer elements arranged linearly along said coordinate axis and being interdigitated with the individual transducer elements of the primary ultrasonic transducer array so that the individual transducer elements of said primary array alternate with the individual transducer elements of said secondary array and so that an individual transducer element of one array is disposed between two individual transducer elements of the other array.

2. An ultrasonic probe according to claim 1 wherein the primary transducer array comprises one of a ceramic, a composite, a semi-composite and a single crystal.

3. An ultrasonic probe according to claim 1 wherein the secondary transducer array comprises one of a ceramic, a composite, a semi-composite and a single crystal.

4. An ultrasonic probe according to claim 1 wherein the primary transducer array and the secondary transducer array are produced from a common piezoelectric member and where each array is of a predetermined thickness corresponding to a respective resonant frequency.

5. An ultrasonic probe according to claim 4 wherein the thickness of the elements of the primary array is determined by cuts formed in the common piezoelectric member and the primary transducer array further comprises electrodes deposited on bottom faces of the elements of the primary array, and a front electrode connected to said electrodes.

6. An ultrasonic probe according to claim 5 wherein the thickness of the elements of the secondary transducer array is determined by portions of the common piezoelectric member remaining after said cuts and the secondary transducer array comprises further electrodes deposited on said remaining portions and a front electrode connected to said further electrodes.

7. An ultrasonic probe according to claim 4 wherein the probe comprises at least two transducer arrays are formed by cuts in a first face and an opposite face of the piezoelectric member.

8. An ultrasonic probe according to claim 4 wherein the resonant frequency of the primary transducer array and the resonant frequency of the secondary transducer array are related by a ratio n, where n is a positive integer.

9. An ultrasonic probe according to claim 1 wherein the primary transducer array comprises a backing providing lateral isolation between the elements of the secondary transducer array.

10. An ultrasonic probe according to claim 1 wherein the elements of the secondary transducer array provide lateral isolation between the elements of the primary transducer array.

11. An ultrasonic probe according to claim 4 wherein the resonant frequency of the primary array transducer and the resonant frequency of the secondary array transducer are related by a ratio different from 1.

12. An ultrasonic probe according to claim 1 wherein the primary transducer array is adapted for use in imaging of the body of a patient and the secondary transducer array is adapted for a simultaneous therapy operation.

13. An ultrasonic probe according to claim 1 wherein the primary transducer array is adapted for use in imaging of the body of patient and the secondary transducer array is adapted for use for a simultaneous Doppler operation.

14. An ultrasonic probe according to claim 1 wherein the primary transducer array is adapted for use for imaging of the body of patient and the secondary transducer array is adapted for use for excitation of non-linear behavior of body tissue so enable the primary transducer array to receive non-linear responses from a portion of the body being imaged.

15. An ultrasonic probe according to claim 1 wherein the primary transducer array is adapted for use in imaging of the body of a patient and the secondary transducer array is adapted for use in delivering drug envelopes incorporated into the patient blood flow.

16. An ultrasonic probe according to claim 1 further including a plurality of insulated attenuating cavities which provide an insulated backing for the transducer elements of the primary array and act as an acoustic barrier for the transducer elements of the secondary array.

17. An ultrasonic probe according to claim 16 wherein said secondary array comprises a piezoelectric member having a rear face and wherein the insulated backing of said primary array has a rear face which is co-planar with the rear face of the piezoelectric member of said secondary array.

18. An ultrasonic probe according to claim 1 wherein said primary and secondary arrays comprise respective piezoelectric members defining a common flat front transceiving surface and a non-uniform rear surface.

19. An ultrasonic linear array transducer according to claim 18 wherein said first sub-array further comprises a first backing member and said second sub-array comprises second, different backing members.

20. An ultrasonic probe design for medical applications, said probe comprising:
(a) a primary ultrasonic transducer array adapted to operate at a first resonant frequency and comprising a plurality of individual transducer elements arranged linearly along an coordinate axis; and
(b) a secondary ultrasonic transducer array adapted to operate at a second resonant frequency and comprising a plurality of individual transducer elements arranged linearly along said coordinate axis and being interdigitated with the individual transducer elements of the primary transducer array so that said individual transducer elements of said primary array alternate with said individual transducer elements of said secondary array and so that an individual transducer element of one army is disposed between two individual transducer elements of the other array;
(c) the secondary transducer array comprising at least one piezoelectric layer abutting a rear face of the primary transducer array.

21. An ultrasonic probe according to claim 20 wherein the elements of secondary transducer array are electrically driven in parallel and layers of piezoelectric material defining the transducer thickness of the secondary transducer array are of inverse polarity.

22. An ultrasonic probe according to claim 20 wherein the piezoelectric layers of the secondary transducer array are of a similar thickness.

23. An ultrasonic probe according to claim 20 wherein the secondary transducer array comprises at least two piezoelectric layers.

24. An ultrasonic probe according to claim 20 wherein the secondary transducer array comprises a first piezoelectric layer having spaced cuts therein along a coordinate axis orthogonal to said one coordinate axis, said first piezoelectric layer having a front surface abutting the primary transducer array and a rear surface; said secondary transducer array further comprising a second piezoelectric layer affixed to the rear surface of the first piezoelectric layer, with only the second piezoelectric layer being electrically addressed and the first piezoelectric layer acting as a matching layer.

25. An ultrasonic probe according to claim 24 wherein the second layer of the secondary transducer array has a resonant frequency such that the thickness of the first layer corresponds to one-half wavelength of said secondary transducer array.

26. An ultrasonic probe according to claim 20 wherein the primary transducer array is adapted for use for imaging of the body of a patient and the secondary transducer array is adapted for administering a simultaneous therapy treatment to the patient.

27. An ultrasonic probe according to claim 20 wherein the primary transducer array is adapted for use for imaging of the body of a patient and the secondary transducer array is adapted for simultaneous Doppler operation.

28. An ultrasonic probe according to claim 20 wherein the primary transducer array is adapted for use for imaging of the body of a patient and the secondary transducer array is adapted for use for excitation of non-linear behavior of tissue so as to enable the primary transducer array to receive non-linear responses a portion of the body being imaged.

29. An ultrasonic probe according to claim 20 wherein the primary transducer array is adapted for use for imaging of the body of the patient and the secondary transducer array is adapted for use for delivering drug envelopes incorporated into the patient blood flow.

30. An ultrasonic linear transducer array for generating and receiving ultrasonic energy, said transducer array comprising:
a first sub-array of individual transducer elements adapted to operate at a first resonance frequency, and with a first bandwidth and having a first circuit interconnect means;
a second sub-array of individual transducer elements interdigitated with the individual transducer elements of the first sub-array so that said individual transducer elements of said first sub-array alternate with said individual transducer elements of said second sub-array and so that an individual transducer element of one array is disposed between two individual transducer elements of the other array, said second sub-array operating at a second resonance frequency, and with a second bandwidth and having a second circuit interconnect means.

31. An ultrasonic linear transducer array according to claim 30 further including a plurality of insulated attenuating cavities which are defined between the transducer elements of the second sub-array behind the transducer elements of the first sub-array and which provide an insulated backing for the first sub-array of transducer elements and act as an acoustic barrier for the second sub-array of transducer elements.

32. An ultrasonic linear array transducer according to claim 31 wherein said second sub-array comprises a piezoelectric member having a rear face and wherein the insulated backing of said first sub-array of transducers has a rear face which is co-planar with the rear face of the piezoelectric member of said second sub-array.

33. An ultrasonic linear transducer array according to claim 30 wherein said first and second sub-arrays comprise respective piezoelectric members defining a common flat front transceiving surface and a non-uniform rear surface.

* * * * *